United States Patent [19]

Braun et al.

[11] 4,418,207

[45] Nov. 29, 1983

[54] ACETYLACETOXYALKYL-ALLYL ETHERS

[75] Inventors: Helmut Braun, Kriftel; Helmut Rinno, Hofheim am Taunus; Karl J. Rauterkus, Kelkheim, all of Fed. Rep. of Germany

[73] Assignee: Hoechst Aktiengesellschaft, Frankfurt am Main, Fed. Rep. of Germany

[21] Appl. No.: 167,004

[22] Filed: Jul. 9, 1980

[30] Foreign Application Priority Data

Jul. 11, 1979 [DE] Fed. Rep. of Germany ....... 2927933

[51] Int. Cl.³ .............................................. C07C 69/72
[52] U.S. Cl. .................................. 560/178; 260/429 J; 524/772; 568/675
[58] Field of Search ................. 560/178, 174; 568/675

[56] References Cited

U.S. PATENT DOCUMENTS

| | | | |
|---|---|---|---|
| 2,167,168 | 7/1939 | Boese, Jr. | 560/178 |
| 3,542,855 | 11/1970 | Moschel | 560/178 |

FOREIGN PATENT DOCUMENTS

| | | |
|---|---|---|
| 2626173 | 12/1977 | Fed. Rep. of Germany. |
| 2628760 | 1/1978 | Fed. Rep. of Germany. |
| 2117571 | 1/1979 | Fed. Rep. of Germany. |
| 39-7758 | 5/1964 | Japan ............................. 568/675 |

*Primary Examiner*—Vivian Garner
*Attorney, Agent, or Firm*—Curtis, Morris & Safford

[57] ABSTRACT

Unsaturated acetoacetic acid esters are suitable as comonomers in the polymerization of unsaturated compounds in an aqueous medium. Particularly suitable are acetylacetoxyalkyl-allyl ethers which may be synthesized in an easy manner and correspond to the formulae

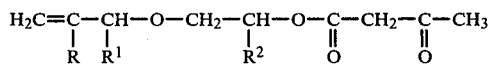

or

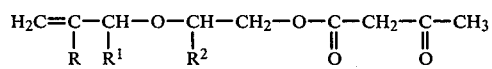

Said allyl ether derivatives are especially prepared by reacting an allyl alcohol with an epoxide and reacting the resulting hydroxyalkyl-allyl ether with diketene. Both reaction steps are carried out at a temperature of from 0° to 100° C., preferably in the presence of a catalyst. The allyl ether derivatives may be copolymerized especially with vinyl compounds, such as vinyl esters, acrylic acid esters, olefins, vinyl halides and vinyl aromatic hydrocarbons.

9 Claims, No Drawings

ACETYLACETOXYALKYL-ALLYL ETHERS

The invention relates to acetylacetoxyalkyl-allyl ethers, their manufacture and their use.

It is known that unsaturated acetoacetic acid esters are suitable comonomers in the polymerization of certain unsaturated compounds (cf. for example British Pat. Nos. 1,541,891 and 1,541,908). The copolymerization is carried out in an aqeous medium, so that an aqueous plastics dispersion is obtained. These plastics dispersions are used as binder dispersions in paints (cf. for example British Pat. No. 1,541,909).

It is the object of the present invention to provide compounds having an olefinically unsaturated double bond and at least one acetoacetyl group, which may be obtained without a high technical expenditure and may be copolymerized with a great number of unsaturated compounds.

The present invention provides acetylacetoxyalkylallyl ethers of formula (I)

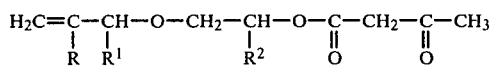

or of formula (II)

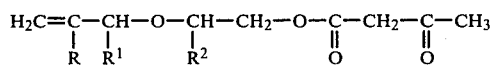

as well as mixtures thereof, in which R is a hydrogen atom or a methyl group, $R^1$ is a hydrogen atom or an alkyl group having 1, 2 or 3 carbon atoms and $R^2$ is a hydrogen atom of a hydrocarbon radical having from 1 to 8 carbon atoms and optionally containing one or several oxygen atoms or a halogen atom. The radical $R^1$ is preferably a hydrogen atom, whereas the radical $R^2$ stands preferably for (a) a hydrogen atom, (b) an alkyl group having 1,2 or 3 carbon atoms which may contain a halogen atom, a hydroxyl group, an acyloxy group having from 3 to 6 carbon atoms or an acetylacetoxy group, or (c) for an aryl group having 6, 7 or 8 carbon atoms.

Hence, the invention relates in particular to acetylacetoxyalkyl-allyl ethers of formula (III)

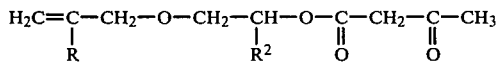

or of formula (IV)

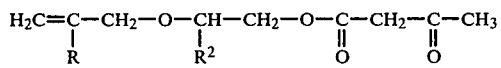

and to mixtures thereof, in which formulae R is a hydrogen atom or a methyl group and $R^2$ is (a) a hydrogen atom, (b) an alkyl group having 1, 2 or 3 carbon atoms, which may be substituted by a halogen atom, preferably a chlorine atom, a hydroxyl radical, an acyloxy radical having from 3 to 6 carbon atoms or an acetylacetoxy group, or (c) an aryl group having 6, 7 or 8 carbon atoms, preferably a phenyl group.

Acetylacetoxyalkyl-(1)-allyl ethers of the invention are, for example, [2-(acetylacetoxy)-ethyl]-(1)-allyl ether, [2-(acetylacetoxy)-ethyl]-(1)-methallyl ether, [2-(acetylacetoxy)-ethyl]-(1)-1-methylallyl ether, [2-(acetylacetoxy)-ethyl]-1-ethylallyl ether, [2-(acetylacetoxy)-ethyl]-1-propyl-(1)-allyl ether, [2-(acetylacetoxy)-propyl]-(1)-allyl ether, [2-(acetylacetoxy)-propyl]-(1)-methallyl ether, [2-(acetylacetoxy)-propyl]-(1)-1-methylallyl ether, as well as [2-(acetylacetoxy)-2-chloromethyl]-ethyl-(1)-ethylallyl ether, [2-(aceetylacetoxy)-2-hydroxymethyl]-ethyl-(1)-allyl ether, [2-(acetylacetoxy)-2-phenyl]-ethyl-(1)-allyl ether, [2-(acetylacetoxy)-2-p-tolyl]-ethyl-(1)-allyl ether, [2,3-bis(acetylacetoxy)-propyl]-(1)-ether, (2-acetylacetoxy-3-acryloyloxy-propyl)-(1)-allyl ether, (2-acetylacetoxy-3-methacryloyloxy-propyl)-(1)-allyl ether and the corresponding methallyl ethers.

The compounds of the invention may be prepared in various ways. For example, a Williamson synthesis may be carried out (a) with an alkali metal salt of an—optionally substituted—(2-hydroxyethyl)-acetoacetic acid ester and an—optionally substituted—allyl halide, or (b) in reverse order with an—optionally substituted—(2-halogenoethyl)-acetoacetic acid ester and an—optionally substituted—alkali-allyl alcoholate. Furthermore, it is possible to prepare first an—optionally substituted—allylglycol ether in analogous manner, to convert the same into the allylglycol-acetic acid ester and to react the latter via a Claisen condensation with acetoacetic acid ethyl ester.

The compounds of the invention may be prepared in a particularly easy and preferred manner by reacting at first an—optionally substituted—allyl alcohol with an epoxide and the resulting hydroxyalkyl-allyl ether with diketene. According to said method, preferably an alcohol of formula (V)

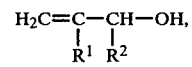

in which $R^1$ and $R^2$ are defined as in formula (I), is at first reacted, under common conditions, with an epoxide of formula (VI)

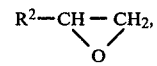

in which $R^2$ is defined as in formula (I), and the resulting hydroxy-alkyl-allyl ether is then reacted with diketene.

As alcohol there is used preferably allyl alcohol or methallyl alcohol; further examples are 1-methylallyl alcohol, 1-ethylallyl alcohol, 1-propylallyl alcohol and 1,2-dimethylallyl alcohol.

Particularly suitable epoxides are those of formula (VI), in which $R^2$ is a hydrogen atom, an alkyl group having 1, 2 or 3 carbon atoms which may be substituted by a halogen atom, preferably a chlorine atom, a hydroxyl radical or an acyl radical having from 3 to 6, preferably 3 or 4 carbon atoms, or stands for an aryl radical having 6, 7 or 8 carbon atoms, preferably a phenyl group. Examples are especially ethylene oxide, propylene oxide, glycide, epichlorohydrin, styrene oxide and glycidyl esters, such as glycidyl acrylate, glycidyl methacrylate and glycidyl crotonate.

The reaction of the alkanol with the epoxide is carried out under common conditions, optionally in the presence of an inert solvent, but preferably in substance. The reaction temperature is in the range of from 0° to 120° C., preferably from 20° to 100° C. The reaction is commonly executed under normal pressure, however, in cases where one of the reactants is present in a gaseous form at the respective reaction temperature, the reaction may also be carried out at elevated pressure. It is performed in the absence of a catalyst or preferably in the presence of a catalyst to be used in an amount of from 0.01 to 2% by weight, preferably from 0.02 to 0.5% by weight (calculated on the total amount of the reactants). As catalysts there may be used in particular substances showing a strongly alkaline reaction, especially (a) alkali metals, such as sodium, potassium and lithium, (b) alkali metal alcoholates, preferably having from 1 to 4 carbon atoms, for example sodium methylate, sodium ethylate, sodium propylate, sodium-t-butylate and the analogous potassium compounds, and especially the alkali metal alcoholates of the unsaturated alcohols used in the respective case, such as sodium allyl alcoholate and sodium methallyl alcoholate, and (c) aliphatic amines, preferably trialkylamines having from 3 to 9 carbon atoms, for example trimethylamine, triethylamine, triethanolamine, and cyclic amines, for example pyridine, piperidine, morpholine and piperazine. There are also suitable compounds with an acid reaction, especially inorganic acids, for example hydrochloric acid, sulfuric acid, nitric acid, phosphoric acid, as well as Lewis acids, for example boron trifluoride and phosphorus trichloride, which may also be employed in the form of their addition compounds, for example as etherates.

The reaction of the hydroxyalkyl-allyl ether obtained in the first reaction step, whose alkyl radical has from 2 to 10 and preferably 2 to 8 carbon atoms and whose allyl radical contains from 3 to 7 and preferably 3 or 4 carbon atoms, with diketene is also carried out under common conditions, optionally in the presence of an inert solvent, but preferably in substance, the reaction temperature being in the range of from 0° to 120° C., preferably from 20° to 100° C. The reaction is normally executed under normal pressure; but elevated pressure may also be applied. It is recommended to effect the reaction in the presence of a catalyst to be used in an amount of from 0.01 to 2% by weight, preferably from 0.02 to 0.5% by weight (calculated on the total amount of the reactants). As catalysts there may be used (a) acids, (b) acidic salts, (c) bases, or (d) basic salts, for example sulfuric acid, phosphoric acid, p-toluene-sulfonic acid, sodium hydrogenosulfate, triethylamine, triethanolamine, and trimethyl ammonium acetate.

The acetylacetoxyalkyl-allyl ethers of the invention are obtained according to the processes described above generally in the form of mixtures of compounds of formula (I) and compounds of formula (II); however, this is not important for the application of the substances of the invention. They may be employed especially as ligand-forming agents for heavy metal ions and as co-monomers in the polymerization of vinyl compounds, such as vinyl esters, acrylic acid esters, olefins, vinyl halides and vinyl aromatic hydrocarbons. The acetylacetoxyalkyl-allyl ethers are preferably employed in the emulsion polymerization of the above-mentioned vinyl compounds.

The following Examples illustrate the invention. The structure of the compounds of the invention was detected in each case by infrared spectrography, the percentages relating to weight.

EXAMPLE 1

(a) 200 Milligrams of pure metallic sodium are added to 58.1 grams (1 mol) of allyl alcohol in a four-necked flask equipped with stirrer, thermometer, dropping funnel and reflux condenser, and the batch is brought to the boil (97° C.). Upon dissolution of the sodium, 61 grams (1.05 mols) of propylene oxide are added constantly, while stirring, to the boiling allyl alcohol within 2 hours. After a subsequent after-reaction period of 1 hour at 97° C. the reaction mixture is distilled at a pressure of 2 millibars. There are obtained 65 grams (55% of the theory) of 2-hydroxy-propyl-(1)-allyl ether having a boiling point of 67° C. at 2 millibars and a refractive index $n_D^{20} = 1.4355$.

(b) 0.03 Gram of trimethylammonium acetate is added to 58.1 grams (0.5 mol) of 2-hydroxypropyl-(1)-allyl ether in the above-described reaction vessel, and the batch is heated to a temperature of 75° C. While maintaining this temperature, 42 grams (0.5 mol) of diketene are added dropwise to the mixture within 30 minutes, while stirring. After a subsequent after-reaction period of 1 hour at 75° C. the reaction mixture is cooled to room temperature. There are obtained 100 grams of 2-acetylacetoxypropyl-(1)-allyl ether as a slightly yellow liquid with a refractive index $n_D^{20} = 1.4450$.

EXAMPLE 2

A mixture of 1,320 grams (10 mols) of 2,3-dihydroxy-propyl-(1)-allyl ether and 9 grams of metallic sodium is heated to 70° C. in a four-necked flask equipped with stirrer, thermometer, dropping funnel and reflux condenser, the sodium thus being dissolved, and while maintaining this temperature, 1,680 grams (20 mols) of diketene are constantly added, while stirring, within 2 hours. After a subsequent after-reaction period of 1 hour at 80° C. the reaction mixture is cooled to room temperature. There are obtained 3000 grams of 2,3-bis-(acetylacetoxy)-propyl-(1)-allyl ether as a yellow oil with a refractive index $n_D^{20} = 1.4625$.

EXAMPLE 3

(a) A mixture of 87 grams (1.5 mols) of allyl alcohol and 1 milliliter of boron trifluoride-diethyl etherate is heated to 60° C. in a reaction vessel provided with reflux condenser, thermometer and dropping funnel. Within 45 minutes, 46.25 grams (0.5 mol) of epichlorohydrin are constantly added to said mixture. The reaction is exothermic. Thereafter the reaction mixture is rectified via a 40 centimeter silver-coated column, whereupon at first 55 grams of unreacted allyl alcohol are distilled off at 24° C. and a pressure of 15 millibars. By subsequent distillation at 0.08 millibars there are obtained 59.7 grams (79.3% of the theory) of (3-chloro-2-hydroxy-propyl)-allyl ether with a boiling point of 57° C. and a refractive index $n_D^{20} = 1.4630$.

(b) A mixture of 37.6 grams (0.25 mol) of (3-chloro-2-hydroxypropyl)-allyl ether and 0.018 grams (0.03%) of trimethylammonium acetate is heated to 75° C. in a four-necked flask equipped with stirrer, thermometer, reflux condenser and dropping funnel. Within 20 minutes, 21 grams (0.25 mol) of diketene are constantly added dropwise to said mixture. The reaction is exothermic. There are obtained 58 grams of (3-chloro-2-acetylacetoxy-propyl)-(1)-allyl ether as a slightly yellowish brown liquid with a refractive index $n_D^{20} = 1.4625$.

EXAMPLE 4

(a) 0.2 Gram of metallic sodium is dissolved in 36 grams (0.5 mol) of butene-(1)-ol-(3) (=1-methylallyl alcohol) in a reaction vessel provided with reflux condenser, thermometer and dropping funnel, and the resulting solution is heated to 60° C. Thereafter 30.5 grams (0.525 mol) of propylene oxide are constantly added within 2.5 hours, whereupon the reaction mixture is maintained at 90° C. for another 2.5 hours. After cooling to room temperature, the mixture is rectified via a 40 centimeter silver-coated column; in this process, 15 grams of unreacted propylene oxide are first distilled off at 35° C. and under normal pressure, and then also 19.6 grams of unreacted butenol at 23° C. and a pressure of 27 millibars. By a further distillation at 27 millibars, 25.1 grams (39.1% of the theory) of (2-hydroxypropyl)-1-methylallyl ether having a boiling point of 62° C. and a refractive index $n_D^{20} = 1.4260$ are obtained.

(b) A mixture of 26 grams (0.2 mol) of (2-hydroxypropyl)-1-methylallyl ether and 0.013 gram (0.03%) of trimethyl ammonium acetate is heated to 75° C. in a four-necked flask equipped with stirrer, reflux condenser, thermometer and dropping funnel. Within 30 minutes, 16.8 grams (0.2 mol) of diketene are constantly added dropwise to said mixture. The reaction is exothermic. There are obtained 43 grams of (2-acetylacetoxypropyl)-(1)-1-methylallyl ether as a slightly brownish liquid with a refractive index $n_D^{20} = 1.4390$.

EXAMPLE 5

(a) A mixture of 87 grams (1.5 mols) of allyl alcohol and 1 milliliter of boron trifluoride-diethyl etherate is heated to 55° C. in a reaction vessel provided with reflux condenser, thermometer and dropping funnel. To this mixture are constantly added 71 grams (0.5 mol) of methacrylic acid-glycidyl ester within 80 minutes. The reaction is exothermic. Subsequently the reaction mixture is rectified via a 40 centimeter silver-coated column, in which process 57 grams of unreacted allyl alcohol are at first distilled off at 25° C. and a pressure of 16 millibars. By a subsequent distillation at 0.3 millibar there are obtained 61.8 grams (61.8% of the theory) of (3-methacryloyloxy-propyl)-allyl ether having a boiling point of 99° C. and a refractive index $n_D^{20} = 1.4120$.

(b) A mixture of 12 grams (0.06 mol) of (3-methacryloyloxy-propyl)-allyl ether and 0.005 gram (0.03%) of trimethyl ammonium acetate is heated to 75° C. in a reaction vessel provided with stirrer, reflux condenser, thermometer and dropping funnel. Within 15 minutes, 5.04 grams (0.06 mol) of diketene are constantly added dropwise to said mixture. The reaction is exothermic. After a subsequent after-reaction period of 1 hour at 80° C. the mixture is cooled to room temperature. There are obtained 17 grams of (2-acetylacetoxy-3-methacryloyloxy-propyl)-(1)-allyl ether as a slightly yellowish brown liquid having a refractive index $n_D^{20} = 1.4255$.

EXAMPLE 6

(a) 4.6 Grams (0.2 mol) of metallic sodium are added portionwise within 3 hours to a solution of 54 grams (0.87 mol) of ethylene glycol and 8 milliliters of absolute toluene in a four-necked flask equipped with stirrer, reflux condenser, thermometer and dropping funnel. Subsequently the mixture is heated until the sodium has melted and is stirred for another 6 hours up to the complete dissolution of the sodium. After decanting the toluene, the flask contents are washed twice with 50 milliliters each of absolute diethyl ether. The remaining sodium glycolate/glycol mixture is heated to 72° C., and with 1 hour 24.4 grams (0.2 mol) of allyl bromide are added in doses. After a subsequent after-reaction period of 1 hour at 110° C. the reaction mixture is rectified via a 40 centimeter silver-coated column. There are obtained 14 grams (68.6% of the theory) of 2-hydroxyethyl-allyl ether having a boiling point of 63° C. at 24 millibars and a refractive index $n_D^{20} = 1.4375$.

A mixture of 12 grams (0.12 mol) of 2-hydroxyethyl-allyl-ether and 0.0065 grams (0.03%) of trimethyl ammonium acetate is heated to 75° C. To this mixture is constantly added dropwise 9.88 grams (0.12 mol) of diketene within 20 minutes, and the mixture is maintained for another hour at 80° C. (exothermic reaction). There are obtained 22 grams of (2-acetylacetoxy-ethyl)-(1)-allyl ether as a slightly yellowish brown liquid with a refractive index $n_D^{20} = 1.4475$.

What is claimed is:

1. Acetylacetoxyalkyl-allyl ether of formula (I)

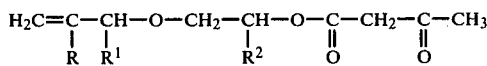

or of formula (II)

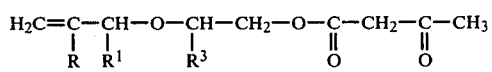

or mixtures thereof, in which R is a hydrogen atom or a methyl group, $R^1$ is a hydrogen atom or an alkyl group having 1, 2 or 3 carbon atoms, $R^2$ is a hydrogen atom, an aryl group having 6 to 8 carbon atoms, or an alkyl group having 1, 2 or 3 carbon atoms unsubstituted or substituted by a halogen atom, a hydroxyl group, or an acyloxy group having from 3 to 6 carbon atoms, and $R^3$ is an aryl group having 6 to 8 carbon atoms, or an alkyl group having 1, 2 or 3 carbon atoms unsubstituted or substituted by a halogen atom, a hydroxyl group or an acyloxy group having from 3 to 6 carbon atoms.

2. The ether of claim 1, which is 2-acetylacetoxypropyl-(1)-allyl ether.

3. The ether of claim 1, which is 2,3-bis(acetylacetoxy)-propyl-(1)-allyl ether.

4. The ether of claim 1, which is (3-chloro-2-acetylacetoxy-propyl)-(1)-allyl ether.

5. The ether of claim 1, which is (2-acetylacetoxypropyl)-(1)-1-methylallyl ether.

6. The ether of claim 1, which is (2-acetylacetoxy-3-methacryloyloxy-propyl)-(1)-allyl ether.

7. The ether of claim 1, which is (2-acetylacetoxyethyl)-(1)-allyl-ether.

8. Acetylacetoxyalkyl-allyl ether of formula (III)

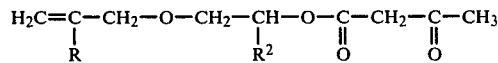

or of formula (IV)

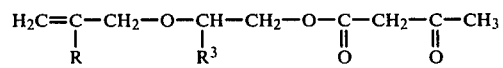

or mixtures thereof, in which R is a hydrogen atom or a methyl group, $R^2$ is (a) a hydrogen atom, (b) an alkyl group having 1, 2 or 3 carbon atoms, unsubstituted or substituted by a halogen atom, a hydroxyl radical or an acyloxy radical having from 3 to 6 carbon atoms or (c) an aryl group having 6, 7 or 8 carbon atoms, and $R^3$ is (a) an alkyl group having 1, 2 or 3 carbon atoms, unsubstituted or substituted by a halogen atom, a hydroxyl radical or an acyloxy radical having from 3 to 6 carbon atoms or (b) an aryl group having 6, 7 or 8 carbon atoms.

9. The ether of claim 8, wherein $R^2$ or $R^3$ is an alkyl of 1, 2 or 3 carbon atoms substituted by an acetylacetoxy.

* * * * *